July 10, 1951 H. F. SMITH Plant Pat. 1,021
PEACH TREE
Filed March 10, 1950
BEST AVAILABLE COPY
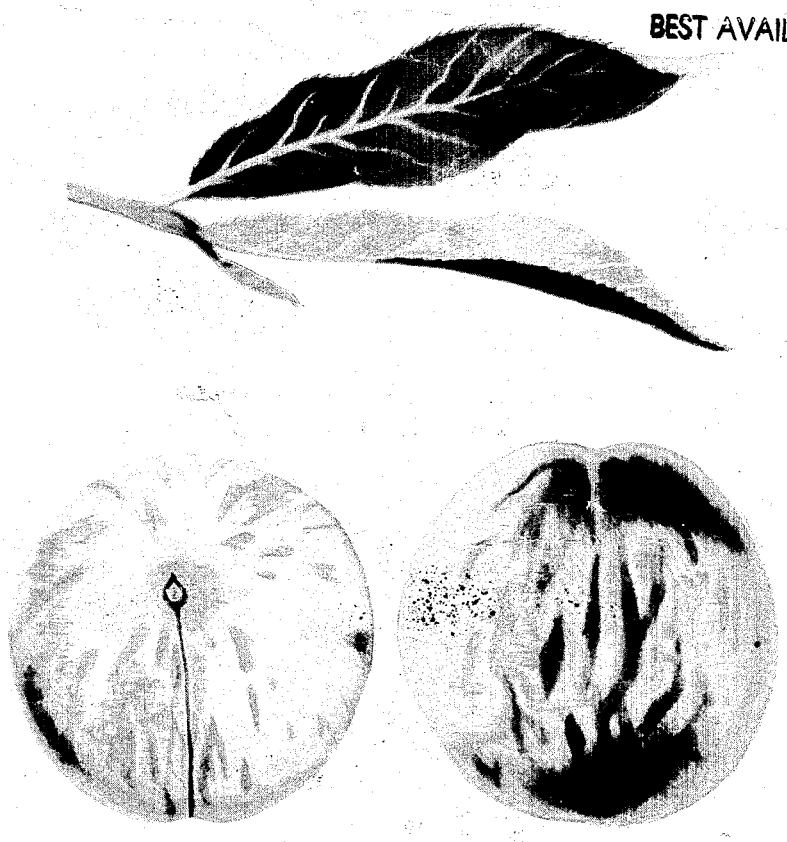
Inventor
Henry Frank Smith
By: J Cobb
Attorneys Patented July 10, 1951

Plant Pat. 1,021

BEST AVAILABLE COPY

UNITED STATES PATENT OFFICE 1,021

PEACH TREE

Henry Frank Smith, Dover, Ark., assignor to Stark Bro's Nurseries and Orchards Company, Louisiana, Mo., a corporation of Missouri Application March 10, 1950, Serial No. 148,688

1 Claim. (Cl. 47—62)

The present discovery relates to a new and distinct variety of peach tree, originating as a bud sport of the variety known as "Fair's Beauty" (unpatented), and discovered by me in my orchard.

This new variety has much the same growing habits and other characteristics of both the tree and the fruit, as the parent variety, but distinctively differs therefrom primarily in the ripening of the fruit of the new variety about two weeks earlier than the fruit of "Fair's Beauty," when grown under comparable conditions.

In another particular, the fruit of the new variety has a somewhat more attractive appearance from the standpoint of color than the fruit of the parent variety, although the difference in color, if any, is usually relatively slight and in general, the new variety may be said to be substantially identical with "Fair's Beauty" except for the earlier maturing characteristic of the new variety as aforementioned.

Asexual reproduction of the new variety by budding at Louisiana, Missouri, shows that the characteristics come true to form and are fixed and transmitted through succeeding propagations.

In the accompanying drawing, [illegible] are depicted specimens of the foliage and [illegible] the fruit of the new variety in plan and in elevation with the coloring thereof as near as can be represented in an illustration, by way of general similarity to the variety "Fair's Beauty" which is not too well-known.

The following [illegible] of the [illegible] cord [illegible] as well as in accordance [illegible] way's Color Standards and Nomenclature of Horticultural Color Guide. Observations were made near Louisiana, Pike County, Missouri.

Dates first and last picking July 14, 1949–July 19, 1949.

*Tree*

Large; vigorous; open [illegible] hardy; productive; regular [illegible]

Trunk: Medium stocky.

Branches: Medium stocky; smooth; glossy. Gray Vinaceous Brown, Plate XXXIX, Colour No. 5''', tone 1, overlaid with Pale Mouse Gray, Plate II, Colour No. 15''''', tone *d* (Ridgway).

*Lenticels.*—Numerous; large.

Leaves: Length, 6¼''; width, 1⅝''. Large; ovate; acutely pointed; thick; smooth; dark green—Spinach Green, Color o960, page 187, volume 2 (Horticultural Color Guide).

*Margin.*—Finely serrate.

*Petiole.*—Short; thick.

*Glands.*—Average number, 3. Alternate; medium small; reniform; free.

Flowers: Dates first and full blossoms—April 12, 1949–April 18, 1949. Medium late; medium small.

*Fruit*

Maturity when described, eating ripe July 15, 1949.

Size: Uniform; large. Axial diameter, 2¾''. Transverse in suture plane, 2¾''. At right angles to suture plane, 2¾''.

Form: Uniform; symmetrical; globose; sides equal.

*Suture.*—Deep; extends from base to beyond apex.

*Ventral surface.*—Strongly lipped toward base throughout both sides; lips, unequal.

*Cavity.*—Abrupt; elongated with suture showing on one side. Markings—none.

*Base.*—Cuneate to rounded.

*Apex.*—Rounded; depressed. Pistil point—apical.

Stem: Length ¼''; stout; glabrous. Adherence [illegible]—medium strong.

[illegible] thick; tough; astringent. Tenacious to flesh—free. Tendency to break—none in wet or dry season.

*Color.*—Highly blushed red and mottled. Blush—Delft Rose Color No. o20/1, page 108, mottled with Oxblood Red Color, oo823, page 191 (Horticultural Color Guide). Down—moderate; medium short; rolls up when rubbed.

*Color.*—[illegible] Color No. 604/1, page [illegible] Horticultural Color Guide. [illegible] with red next [illegible] Color No. 18/1, page [illegible] Horticultural Color Guide. [illegible] pit cavity, Yellow—Mimeso Yellow No. 602/3, page 143, volume 2, [illegible] Horticultural Color Guide.

BEST AVAILABLE COPY

*Amygadalin.*—Wanting. Juice—abundant; rich.
*Texture.*—Firm.
*Fibres.*—Few; fine; tender.
*Ripens.*—Fairly even; earliest along large lips.
*Flavor.*—Mild.
*Aroma.*—Distinct.
*Eating quality.*—Good.

Stone: Semi-cling; adheres to flesh along both dorsal and ventral edges and over upper half of sides.
*Fibres.*—Long.
*Size.*—Medium small; length 1⅝"; thickness ¾".
*Form.*—Oval; cuneate toward base.
*Base.*—Oblique. Hilum—narrow; oval. Apex—acute.
*Sides.*—Equal; curved on right and left sides.
*Surface.*—Irregularly furrowed near base; pitted from base to above center.

*Ridges.*—Ragged toward base.
*Pits.*—Circular; ventral edge thick with wing throughout.
*Dorsal edge.*—Narrow with deep narrow groove throughout. Ridges—on either side interrupted.

Use: Market; dessert.
Keeping quality: Medium good.
Resistance to:
*Insects.*—Good.
*Diseases.*—Good.
Shipping quality: Good.

I claim:

A new and distinct variety of peach tree, characterized by its similarity to the variety "Fair's Beauty," while differing therefrom primarily by the earlier ripening period of its fruit, substantially as shown and described.

HENRY FRANK SMITH.

No references cited.